United States Patent [19]
Woulfe

[11] Patent Number: 5,888,476
[45] Date of Patent: Mar. 30, 1999

[54] MAGNETIC RESONANCE BLOOD POOL AGENTS

[75] Inventor: Steven R. Woulfe, Ballwin, Mo.

[73] Assignee: Mallinckrodt Medical, Inc., St. Louis, Mo.

[21] Appl. No.: 748,302

[22] Filed: Nov. 13, 1996

[51] Int. Cl.⁶ .......................... A61K 49/00; G01N 31/00; G01N 33/48
[52] U.S. Cl. ..................... 424/9.364; 424/1.65; 424/9.1; 424/9.3; 534/10; 534/14; 534/15
[58] Field of Search .................................. 534/10, 14, 15, 534/16; 424/1.65, 9.363, 9.364, 9.365, 9.1, 9.3

[56] References Cited

U.S. PATENT DOCUMENTS

| | | | |
|---|---|---|---|
| 4,826,673 | 5/1989 | Dean et al. | 424/9 |
| 4,885,363 | 12/1989 | Tweedle et al. | 540/465 |
| 5,011,925 | 4/1991 | Rajagopalan et al. | 544/58.1 |
| 5,137,711 | 8/1992 | Weber et al. | 424/9 |
| 5,138,040 | 8/1992 | Moore et al. | 534/16 |
| 5,324,503 | 6/1994 | Lin et al. | 424/5 |
| 5,562,894 | 10/1996 | White | 424/9.365 |
| 5,573,752 | 11/1996 | Ranganathan et al. | 424/9.363 |
| 5,575,986 | 11/1996 | Mori et al. | 424/9.364 |
| 5,582,814 | 12/1996 | Scott et al. | 424/9.364 |

*Primary Examiner*—John Kight
*Assistant Examiner*—Dameron Jones
*Attorney, Agent, or Firm*—Wendell Ray Guffey; Brian K. Stierwalt

[57] ABSTRACT

The present invention provides compositions comprising contrast agents capable of binding non-covalently to blood proteins. The compositions of the invention provide increased residence time of contrast agents in the vasculature, thus providing effective blood pool contrast agents. The invention also provides methods for imaging a patient comprising administering a composition of the invention to a patient and obtaining an image.

12 Claims, 1 Drawing Sheet

MAGNETIC RESONANCE BLOOD POOL AGENTS

FIELD OF THE INVENTION

The invention is in the field of imaging. Particularly, the invention is in the magnetic resonance imaging (MRI) field. And most particularly, the invention is in the field of MRI of the blood pool.

BACKGROUND OF THE INVENTION

The use of contrast agents in diagnostic medicine is rapidly growing. In conventional proton magnetic resonance imaging (MRI) diagnostics, increased contrast of internal organs and tissues may be obtained by administering compositions containing paramagnetic metal species which increase the relaxivity of water protons surrounding the tissue.

The technique of MRI encompasses the detection of certain atomic nuclei utilizing magnetic fields and radio-frequency radiation. It is similar in some respects to X-ray computed tomography (CT) in providing a cross-sectional display of the body organ anatomy with excellent resolution of soft tissue detail. As currently used, the images produced constitute a map of the proton density distribution, in organs and tissues. The technique of MRI is advantageously non-invasive as it avoids the use of ionizing radiation.

While the phenomenon of NMR was discovered in 1945, its potential use as MRI agent to map the internal structure of the body was originally suggested by Lauterbur in 1973. (Nature, 242, 190–191 [1973]). The fundamental lack of any known hazard associated with the level of the magnetic field and radio-frequency wave that are employed renders it possible to make repeated scans on vulnerable individuals. In addition to standard scan planes (axial, coronal, and sagittal), oblique scan planes can also be selected.

With an MRI experiment, the nuclei under study in a sample (e.g. protons) are irradiated with the appropriate radio-frequency (RF) energy in a highly uniform magnetic field. These nuclei, as they relax, subsequently emit RF at a sharp resonance frequency. The resonance frequency of the nuclei depends on the applied magnetic field.

According to known principles, nuclei with appropriate spin, when placed in an applied magnetic field (B, expressed generally in units of gauss or Tesla [$10^4$ gauss]) align in the direction of the field. In the case of protons, these nuclei precess at a frequency, f, of 42.6 MHz, at a field strength of 1 Tesla. At this frequency, an RF pulse of radiation will excite the nuclei and can be considered to tip the net magnetization out of the field direction, the extent of this rotation being determined by the pulse duration and energy. After the RF pulse, the nuclei "relax" or return to equilibrium with the magnetic field, emitting radiation at the resonant frequency. The decay of the emitted radiation is characterized by two relaxation times, i.e., $T_1$, the spin-lattice relaxation time or longitudinal relaxation time, that is, the time taken by the nuclei to return to equilibrium along the direction of the externally applied magnetic field, and $T_2$, the spin-spin relaxation time associated with the dephasing of the initially coherent precession of individual proton spins. These relaxation times have been established for various fluids, organs and tissues in different species of mammals.

In MRI, scanning planes and slice thicknesses can be selected. This selection permits high quality transverse, coronal and sagittal images to be obtained directly. The absence of any moving parts in MRI equipment promotes high reliability. It is believed that MRI has a greater potential than CT for the selective examination of tissue characteristics in view of the fact that in CT, X-ray attenuation coefficients alone determine image contrast, whereas at least five separate variables ($T_1$, $T_2$, proton density, pulse sequence and flow) may contribute to the MRI signal.

By reason of its sensitivity to subtle physico-chemical differences between organs and/or tissues, it is believed that MRI may be capable of differentiating different tissue types and in detecting diseases which induce physicochemical changes that may not be detected by X-ray or CT which are only sensitive to differences in the electron density of tissue.

As noted above, two of the principal imaging parameters are the relaxation times, $T_1$ and $T_2$. For protons (or other appropriate nuclei), these relaxation times are influenced by the environment of the nuclei, (e.g., viscosity, temperature, and mechanisms whereby the initially imparted radio-frequency energy is dissipated to the surrounding environment. The rate of this energy loss or relaxation can be influenced by certain other nuclei which are paramagnetic. Chemical compounds incorporating these paramagnetic nuclei may substantially alter the $T_1$ and $T_2$ values for nearby protons. The extent of the paramagnetic effect of a given chemical compound is a function of the environment.

Typically, paramagnetic ions have been administered in the form of complexes with organic complexing agents. Such complexes provide the paramagnetic ions in a soluble, non-toxic forms, and facilitate their rapid clearance from the body following the imaging procedure. Gries, et al., U.S. Pat. No. 4,647,447, disclose complexes of various paramagnetic ions with conventional aminocarboxylic acid complexing agents. A preferred complex disclosed by Gries, et al. is the complex of gadolinium (III) with diethylenetriaminepentaacetic acid ("DTPA").

With acceptance and widespread use of MRI, new needs for contrast agents arise. Historically, in the field of MR contrast agent development, efforts to produce such agents have primarily focused upon derivatizing polymers with relaxation agents (e.g. Gd-DTPA polylsine) as well as polyethylene glycol-or carbohydrate-coated paramagnetic or supermagnetic particles. Such agents have not found widespread use because they remain indefinitely in the vasculature or present significant physiological side effects. Clinicians have repeatedly expressed their desire for contrast agents that remain concentrated in the blood, versus surrounding tissue, for extended periods of time.

SUMMARY OF THE INVENTION

The invention provides compositions comprising the general formula (I):

wherein A is a mono or polycyclic $C_6$–$C_{20}$ alkyl group, optionally substituted with one or more —$NH_2$, —$CO_2H$, —$SO_3H$ or —$PO_3H_2$ groups; B is a chelate; L is a linker between A and B corresponding to a group of formula (II):

in which n is an integer from about zero to about 6; $R_1$, $R_2$ and $R_3$ may be the same or different and are hydrogen or —$(CH_2)_m$—X; m is an integer from about zero to about 6;

X is hydrogen, —NH$_2$, —CO$_2$H, —SO$_3$H or —PO$_3$H$_2$; and B is a chelating agent of metal ions having atomic numbers varying from 22 to 29, 42 to 44 and 58 to 70.

The invention also provides compositions comprising the general formula (I):

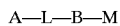 (I)

wherein A is a mono or polycyclic C$_6$–C$_{20}$ alkyl group, optionally substituted with one or more —NH$_2$, —CO$_2$H, —SO$_3$H or —PO$_3$H$_2$ groups; B is a chelate; L is a linker between A and B corresponding to a group of formula (II):

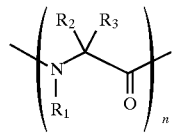 (II)

in which n is an integer from about zero to about 6; R$_1$, R$_2$ and R$_3$ may be the same or different and are hydrogen or —(CH$_2$)$_m$—X; m is an integer from about zero to about 6; X is hydrogen, —NH$_2$, —CO$_2$H, —SO$_3$H or —PO$_3$H$_2$; B is a chelating agent of M; and M is a metal ion having an atomic number varying from 22 to 29, 42 to 44 and 58 to 70.

The present invention provides compositions comprising contrast agents capable of binding non-covalently to blood proteins. The compositions of the invention provide increased residence time of contrast agents in the vasculature, thus providing effective blood pool contrast agents. The invention also provides methods for imaging a patient comprising administering a composition of the invention to a patient and obtaining an image.

DETAILED DESCRIPTION OF INVENTION

Figure 1:
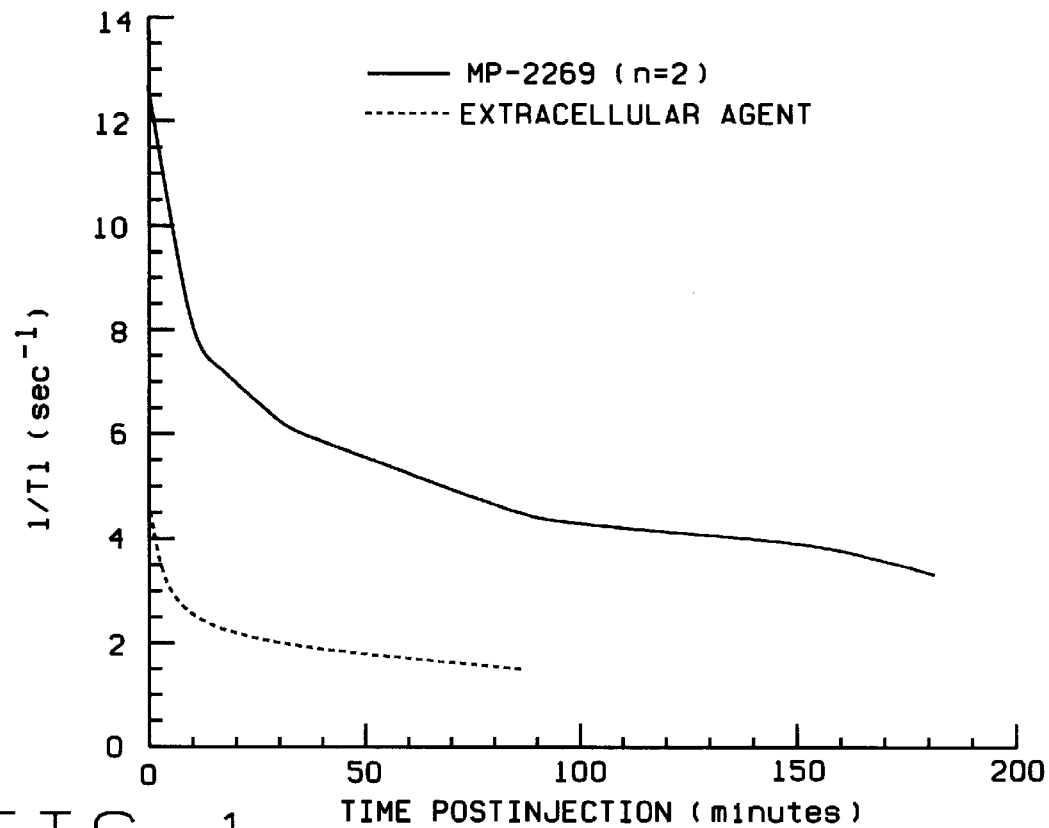

The high concentration of human serum albumin (HSA) in the blood, coupled with its propensity for binding non-covalently with a variety of endogenous and exogenous molecules with a relatively high affinity, make it a good target for MR blood pool agents. HSA is typically found in the blood stream at a concentration of 0.68 mM. Assuming that binding of a small gadolinium chelate to HSA will result in an increase in relaxivity to approximately 20 mM$^{-1}$sec$^{-1}$, initial calculations indicate that a concentration of 0.2 mM in bound gadolinium chelate will be required to provide effective contrast. This indicates that targeting of a small gadolinium chelate to HSA will require only one to one binding with no amplification of the number of gadolinium atoms per targeting group.

HSA is a transport protein known for its ability to bind reversibly with a variety of ligands (Meyer, M. C.; Guttman, D. E. *Journal of Pharmaceutical Sciences* 1968, 57, 895. Kragh-Hansen, U. *Pharmacological Reviews* 1981, 33, 17. Kragh-Hansen, U. *Danish Medical Bulletin* 1990, 37, 57). A great deal of HSA binding information was gleaned from it's recently obtained x-ray crystal structure (He, X. M.; Carter, D. C. *Nature* 1992, 358, 209. Carter, D. C.; Ho, J. X. *Adv. Protein Chemistry* 1994, 45, 153).

There are six principle binding locations on albumin, two each for metals, long-chain fatty acids and small aromatic molecules. The two metal binding sites are the cysteine residue at position 34 and the N-terminus. There are two high affinity and approximately four lower affinity binding sites for long-chain fatty acids. Their location is not precisely known but 1–2 fatty acids are typically bound to circulating albumin. Binding affinities of palmitate (C$_{16}$), stearate (C$_{18}$) and oleate (C$_{20}$) are high with a value of 10$^7$–10$^8$M$^{-1}$. HSA possesses two binding sites for small aromatic molecules. Each site has similar, but not identical, properties and prefers small heterocyclic or carbocyclic aromatic carboxylic acids. A short list of both endogenous and exogenous molecules and their binding affinities (K) to HSA are shown below.

| Compound | K (M$^{-1}$) |
|---|---|
| Bilirubin | 10$^8$ |
| Hematin | 10$^8$ |
| Steroids | 10$^4$–10$^7$ |
| L-Thyroxine | 10$^6$ |
| L-Tyrptophan | 10$^4$ |
| Phenyl butazone | 10$^5$ |
| Warfarin | 10$^5$ |
| Ibuprofen | 10$^6$ |

It is readily apparent that small gadolinium chelates with appropriate pendant functionality such as fatty acids and aromatic carboxylic acids, that can bind strongly but reversibly to HSA in vivo could afford effective MR blood pool agents.

The compositions of the invention are paramagnetic chelates that possess non-aryl, lipophilic HSA targeting moieties. Such chelates are capable of binding strongly but reversibly to HSA in vivo. The compositions of the invention provide increased residence time of the contrast agent in the vasculature, thus providing effective blood pool contrast agents.

Examples of suitable mono or polycyclic C$_6$–C$_{20}$ alkyl groups for use with the invention include 4-pentylbicyclo[2.2.2]octane-1-carboxylic acid, adamantane-1-carboxylic acid, adamantane-1,3-dicarboxylic acid, 1-amino-adamantane-3-carboxylic acid and dicyclohexylacetic acid. Suitable linker groups include aspartic acid, diaspartic acid, triaspartic acid, glutamic acid, diglutamic acid and tri-glutamic acid. Suitable chelate groups include gadolinium (III)-diethylenetriaminepentaacetic acid (DTPA), gadolinium(III)-1,4,7,10-tetraazacyclododecane-1,4,7,10-tetraacetic acid (DOTA) and manganese(II)-ethylenediaminetetraacetic acid (EDTA).

The chelating group can be attached to the linker by means of a reactive group present on the chelate. Typically, a nucleophilic group is reacted with an electrophilic group to form a covalent bond. Examples of nucleophilic groups include amines, anilines, alcohols, phenols, thiols and hydrazines. Electrophilic groups include halides, disulfides, anhydrides, activated esters, imidates, isocyanates and isothiocyanates. Similar means can be used to attach the targeting group to the linker.

Examples of preferred compounds of the invention include gadolinium(III)-4-pentylbicyclo[2.2.2]octane-1-carboxyl-L-aspartyl-L-aspartyl-4-aminobutyl-diethylenetriaminepentaacetic acid, gadolinium(III)-3-carboxy-adamantane-1-carboxyl-L-aspartyl-4-aminobutyl-diethylenetriaminepentaacetic acid, gadolinium(III)-dicyclohexylacetyl-L-aspartyl-4-aminobutyl-diethylenetriaminepentaacetic acid, gadolinium(III)-4-pentylbicyclo[2.2.2]octane-1-carboxyl-L-aspartyl-L-aspartyl-4-aminobutyl-1,4,7,10-tetraazacyclododecane-1,4,7,10-tetraacetic acid, and gadolinium (III)-4-pentylbicyclo[2.2.2]octane-1-carboxyl-L-N-methyl-aspartyl-L-N-methyl-aspartyl-4-N-methyl-aminobutyl-diethylenetriaminepentaacetic acid.

The compositions of the invention are capable of binding non-covalently to blood proteins (Table 1 and 2). The large increase in relaxivity observed in HSA solutions and human blood are indicative of strong binding of the agents to large proteins. This is due to an alteration in the effective correlation time of the electron-nuclear interaction as a result of binding to large macromolecules (proteins).

TABLE 1

In Vitro Relaxivity ($R_1$) Values of Gadolinium(III)-4-pentylbicyclo[2.2.2]octane-1-carboxyl-4-aminobutyldiethylenetriaminepentaacetic acid.

| Matrix | $R_1$ (mM$^{-1}$sec$^{-1}$) |
|---|---|
| Water | 5.0 |
| Human Albumin | 24.3 |
| Human Blood | 23.0 |

TABLE 2

In Vitro Relaxivity ($R_1$) Values of Gadolinium(III)-4-pentylbicyclo[2.2.2]octane-1-carboxyl-L-aspartyl-L-aspartyl-4-aminobutyldiethylenetriaminepentaacetic acid.

| Matrix | $R_1$ (mM$^{-1}$sec$^{-1}$) |
|---|---|
| Water | 6.2 |
| Human Albumin | 17.1 |
| Human Blood | 26.0 |

Figure 2:
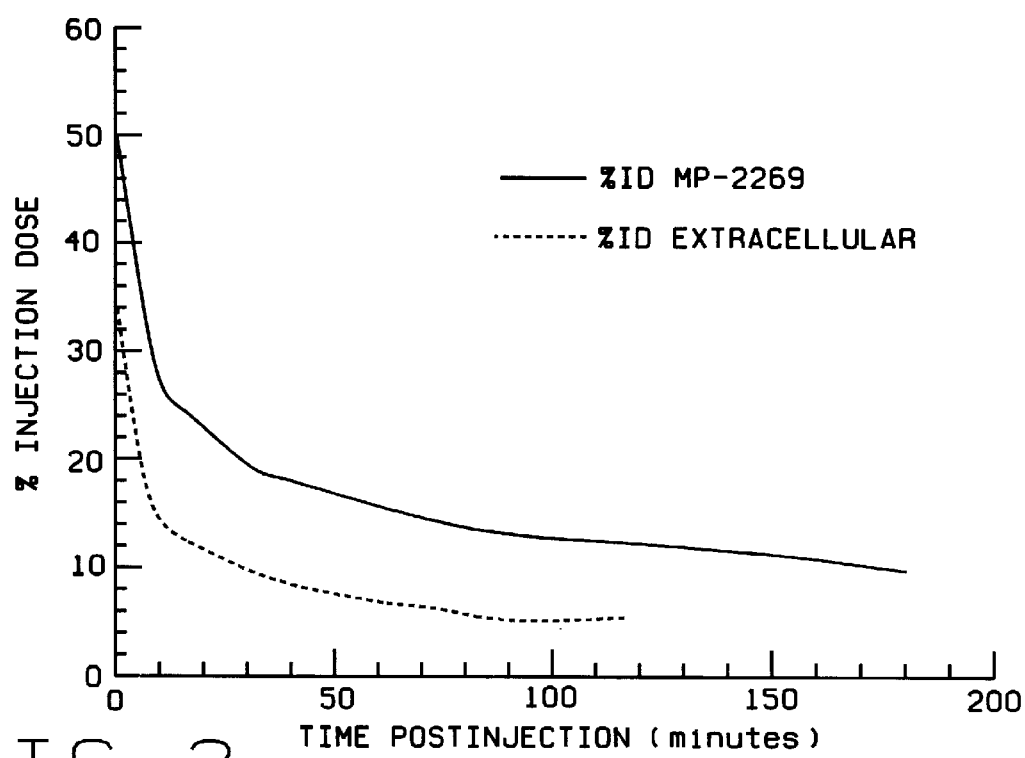

The compositions of the invention are capable of in vivo binding to blood proteins (FIGS. 1 and 2). The invention provides agents with increased residence time in the vasculature, thus providing effective blood pool contrast agents.

BRIEF DESCRIPTION IF THE DRAWINGS

FIG. 1. T1(1/T1) vs. Time Postinjection of a Single Bolus (45 μmol/kg) of Gladolinium(III)-4-pentylbicyclo[2.2.2]octane-1-carboxyl-L-aspartyl-L-aspartyl-4-aminobutyldiethylenetriaminepentaacetic acid (MP-2269) in a Rabbit.

FIG. 2. % Injected Dose (ID) vs. Time Postinjection of a Single Bolus (45 μmol/kg) of Gadolinium(III)-4-pentylbicyclo[2.2.2]octane-1-carboxyl-L-aspartyl-L-aspartyl-4-aminobutyldiethylenetriaminepentaacetic acid in a Rabbit.

In general, paramagnetic species such as ions of elements with atomic numbers of 22 to 29, 42 to 44 and 58 to 70 have been found effective as MRI image contrasting agents. Examples of suitable ions include chromium(III), manganese(II), manganese(III), iron(II), iron(III), cobalt(II), nickel(II), copper(II), praseodymium(III), neodymium(III), samarium(III), and ytterbium(III). Because of their very strong magnetic moments, gadolinium(III), terbium(III), dysprosium(III), holmium(III) and erbium(III) are preferred. Gadolinium(III) ions have been particularly preferred as MRI contrasting agents.

The compositions of the invention can be formulated into diagnostic compositions for enteral or parenteral administration. These compositions contain an effective amount of the paramagnetic ion complex along with conventional pharmaceutical carriers and excipients appropriate for the type of administration contemplated. For example, parenteral formulations advantageously contain a sterile aqueous solution or suspension of from about 0.05 to about 1.0M of a paramagnetic ion complex according to this invention. Parenteral compositions may be injected directly or mixed with a large volume parenteral composition for systemic administration. Preferred parenteral formulations have a concentration of paramagnetic ion complex of about 0.1M to about 0.5M. Such solutions also may contain pharmaceutically acceptable buffers and, optionally, electrolytes such as sodium chloride. The compositions may advantageously contain a slight excess (e.g., from about 0.01 to about 15.0 mole % excess) of a complexing agent or its complex with a physiologically acceptable, non-toxic cation. Such physiologically acceptable, non-toxic cations include calcium ions, magnesium ions, copper ions, zinc ions, salts of n-methylglucamine and diethanolamine, and the like. Generally, calcium ions are preferred.

Formulations for enteral administration may vary widely, as is well-known in the art. In general, such formulations are liquids which include an effective amount of the paramagnetic ion complex in aqueous solution or suspension. Such enteral compositions may optionally include buffers, surfactants, thixotropic agents, and the like. Compositions for oral administration may also contain flavoring agents and other ingredients for enhancing their organoleptic qualities.

The diagnostic compositions are administered in doses effective to achieve the desired enhancement of the NMR image. Such doses may vary widely, depending upon the particular paramagnetic ion complex employed, the organs or tissues which are the subject of the imaging procedure, the NMR imaging procedure, the NMR imaging equipment being used, and the like. In general, parenteral dosages will range from about 0.001 to about 1.0 MMol of paramagnetic ion complex per kg of patient body weight. Preferred parenteral dosages range from about 0.01 to about 0.5 MMol of paramagnetic ion complex per kg of patient body weight. Enteral dosages generally range from about 0.5 to about 100 MMol, preferably from about 1.0 to about 10 MMol, preferably from about 1.0 to about 20.0 MMol of paramagnetic ion complex per kg of patient body weight.

The diagnostic compositions of the invention are used in the conventional manner. The compositions may be administered to a patient, typically a warm-blooded animal, either systemically or locally to the organ or tissue to be imaged, and the patient then subjected to the NMR imaging procedure. Protocols for imaging and instrument procedures are found in texts such as Stark, D. D.; Bradley, W. G. *Magnetic Resonance Imaging*; Mosby Year Book: St. Louis, Mo., 1992.

The following examples illustrate the specific embodiments of the invention described in this document. As would be apparent to skilled artisans, various changes and modifications are possible and are contemplated within the scope of the invention described.

EXAMPLES

Example 1

Synthesis of gadolinium(III)-4-pentylbicyclo[2.2.2]octane-1-carboxyl-4-aminobutyl-diethylenetriaminepentaacetic acid.

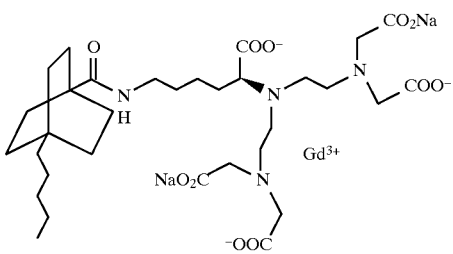

A mixture of 4-pentylbicyclo[2.2.2]octane-1-carboxylic acid (1.7 g, 7.5 mmol), N-hydroxysuccinimide (863 mg, 7.5 mmol) and dicyclohexylcarbodiimide (1.5 g, 7.5 mmol) in 10 mL of DMF and 10 mL of methylene chloride was stirred at room temperature for 3 hours. The precipitated dicyclohexylurea was removed by filtration and the filtrate evaporated. The residue was diluted with 20 mL of methylene chloride. A solution of 4-aminobutyl-diethylenetriaminepentaacetic acid penta-t-butyl ester (5.6 g, 7.5 mmol, prepared as outlined in Williams, M. A.; Rapoport, H. *J Org. Chem* 1993, 58, 1151 ) in 10 mL of methylene chloride was added. The mixture was stirred for two hours at room temperature. The solvent was evaporated and the residue was chomatographed on silica gel (ethyl acetate/hexanes) to afford 3.0 g (42%) of 4-pentylbicyclo[2.2.2]octane-1-carboxyl-4-aminobutyl-diethylenetriaminepentaacetic acid penta-t-butyl ester as a colorless oil. $^1$H NMR, $^{13}$C NMR and MS consistent.

A solution of 4-pentylbicyclo[2.2.2]octane-1-carboxyl-4-aminobutyl-diethylenetriaminepentaacetic acid penta-t-butyl ester (2.4 g, 2.5 mmol) in 10 mL of dioxane and 10 mL of 12N HCl was stirred at room temperature for two hours. The solvents were evaporated and the residue was chromatographed on $C_{18}$ (water/acetonitrile) to afford 1.5 g (78%) of 4-pentylbicyclo[2.2.2]octane-1-carboxyl-4-aminobutyl-diethylenetriaminepentaacetic acid trihydrochloride salt as a white powder. $^1$H NMR, $^{13}$C NMR and MS consistent.

A solution of 4-pentylbicyclo[2.2.2]octane-1-carboxyl-4-aminobutyl-diethylenetriaminepentaacetic acid trihydrochloride salt (382 mg, 0.49 mmol) in water (5 mL) was adjusted to pH 5 with 1N sodium hydroxide. In a separate flask, 1N hydrochloric acid (1.5 mL, 1.5 mmol) was added to gadolinium oxide (800 mg, 0.22 mmol) and water was added to bring the volume up to 5 mL. This mixture was heated to 60 degrees C. until all solids dissolved. The resulting gadolinium chloride solution was added dropwise to the ligand and the mixture was vigorously stirred while maintaining a pH of 6–7 with 1N sodium hydroxide. After the addition was complete, the pH was adjusted to 7.4 with 1N sodium hydroxide to give an aqueous solution of gadolinium(III)-4-pentylbicyclo[2.2.2]octane-1-carboxyl-4-aminobutyl-diethylenetriaminepentaacetic acid. MS consistent.

Example 2

Synthesis of gadolinium(III)-4-pentylbicyclo[2.2.2]octane-1-carboxyl-L-aspartyl-L-aspartyl-4-aminobutyl-diethylenetriaminepentaacetic acid.

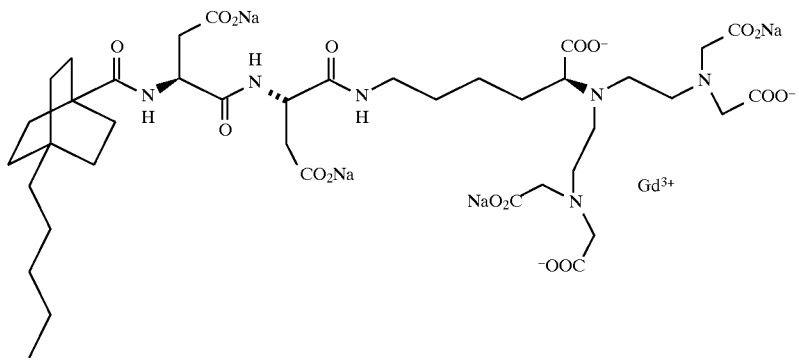

In a flask equipped with a condenser fitted with a drierite drying tube was placed 4-pentylbicyclo[2.2.2]octane-1-carboxylic acid (10 g, 0.045 mol). Thionyl chloride (52.2 g, 32.0 mL, 0.44 mol) was added and the slurry was slowly heated to reflux in an oil bath. Reflux was maintained for 3 hrs and then the solvent was removed under reduced pressure. Anhydrous toluene (40 mL) was added and the solvents were again evaporated. The resulting oil was dissolved in anhydrous dioxane (50 mL) and added to a slurry of L-aspartic acid β-t-butyl ester (10.1 g, 0.054 mol), sodium bicarbonate (4.9 g, 0.058 mol) and diisopropylethylamine (7.5 g, 10.1 mL, 0.058 mol) in 1,4-dioxane (100 mL) and water (50 mL). The mixture was stirred at 25° C. for 15 hrs. The pH of the mixture was adjusted to 3 with concentrated hydrochloric acid and diluted with diethyl ether (200 mL). The layers were separated and the aqueous layer was reextracted with ether. The organic layer was washed with 100 L of 10% hydrochloric acid, dried over anhydrous sodium sulfate and evaporated under reduced pressure. The oil was crystallized from acetonitrile to give 4-pentylbicyclo[2.2.2]octane-1-(L-β-t-butylaspartyl)carboxyamide(15.3 g, 0.039 mol, 87%).

A mixture of 4-pentylbicyclo[2.2.2]octane-1-(L-β-t-butylaspartyl)carboxyamide (10.0 g, 0.025 mol), N-hydroxysuccinimide (3.2 g, 0.028 mol) and dicyclohexylcarbodiimide (5.7 g, 0.028 mol) in anhydrous 1,4-dioxane (250 mL) was stirred at 25° C. for 15 hrs. The solid was removed by filtration and the filtrate was evaporated to near dryness under reduced pressure. The residue was partitioned between diethyl ether (200 mL) and washed successively with 100 mL of saturated sodium bicarbonate and 100 mL of saturated sodium chloride. The organic solution was dried over anhydrous sodium sulfate and stripped under reduced pressure. The crude active ester was then dissolved in 1,4-dioxane (150 mL) and added to a mixture of L-aspartic acid β-t-butyl ester (5.7 g, 0.030 mol), sodium bicarbonate (2.8 g, 0.033 mol) and diisopropylethylamine (4.2 g, 5.7 mL, 0.030 mol) in 1,4-dioxane (100 mL). The mixture was stirred at 25° C. for 15 hrs. The pH of the solution was adjusted to 3 with concentrated hydrochloric acid and then diluted with diethyl ether (300 mL). The layers were separated and the aqueous layer was extracted with diethyl ether (100 mL). The combined organic layers were washed with 100 mL of 10% hydrochloric acid, dried over anhydrous sodium sulfate and evaporated under reduced pressure to give 4-pentylbicyclo[2.2.2]octane-1-di-(L-β-t-butylaspartyl)carboxyamide as an oil. This material was used without further purification.

The above crude 4-pentylbicyclo[2.2.2]octane-1-di-(L-β-t-butylaspartyl)carboxyamide (5.0 g, 8.80 mmol) was stirred with N-hydroxysuccinimide (1.1 g, 9.70 mmol) and dicyclohexylcarbodiimide (2.0 g, 9.70 mmol) in anhydrous 1,4-dioxane (80 mL) at 25° C. for 15 hrs. The solids were removed by filtration and the filtrate was evaporated under reduced pressure. Diethyl ether (200 mL) was added to dissolve the oil and the solution was washed with 100 mL of saturated sodium bicarbonate, dried over anhydrous sodium sulfate and evaporated under reduced pressure. The resulting crude active ester was dissolved in anhydrous 1,4-dioxane (50 mL) and added to a solution of 4-aminobutyl-diethylenetriaminepentaacetic acid penta-t-butyl ester (6.8 g, 9.2 mmol) in anhydrous 1,4-dioxane (20 mL). The solution was stirred at 25° C. for 15 hrs. Then diethyl ether (200 mL) was added and the solution was washed successively with 100 mL each of 10% hydrochloric acid, saturated sodium bicarbonate and saturated sodium chloride. The organic layer was dried over anhydrous sodium sulfate and stripped to an oil under reduced pressure. The crude material was purified via silica gel chromatography using a methanol/dichloromethane gradient as eluant. Pure fractions were combined to give 4-pentylbicyclo[2.2.2]octane-1-carboxyl-di-L-aspartyl-4-aminobutyl-diethylenetriaminepentaacetic acid hepta-t-butyl ester (5.9 g, 4.6 mmol, 52%). $^1$H NMR, $^{13}$C NMR and MS consistent.

A solution of 4-pentylbicyclo[2.2.2]octane-1-carboxyl-di-L-aspartyl-4-aminobutyl-diethylenetriaminepentaacetic acid hepta-t-butyl ester (4.5 g, 3.5 mmol) in concentrated hydrochloric acid (11 mL) and anhydrous 1,4-dioxane (11 mL) was stirred at 25° C. for 15 hrs. The solvents were removed under reduced pressure and the residue was taken up in 5 mL of water. The water was stripped carefully (foaming occurred) under reduced pressure to give a gum. Acetonitrile was added to the gum until solids formed and then the solvent was decanted. The solid was triturated with acetone, filtered and dried to give 4-pentylbicyclo[2.2.2] octane-1-carboxyl-di-L-aspartyl-4-aminobutyl-diethylenetriaminepentaacetic acid trihydrochloride as a white powder (3.0 g, 2.9 mmol, 86%). $^1$H NMR, $^{13}$C NMR and MS consistent.

A suspension of 4-pentylbicyclo[2.2.2]octane-1-carboxyl-di-L-aspartyl-4-aminobutyl-diethylenetriaminepentaacetic acid trihydrochloride (0.50 g, 0.49 mmol) in water (5 mL) was adjusted to pH 5 with 1N sodium hydroxide and stirred until the solids dissolved. Then 1N hydrochloric acid (1.5 mL, 1.5 mmol) was added to gadolinium oxide (0.80 g, 0.22 mmol) and water was added to bring the volume up to 5 mL. This mixture was heated at 60° C. until all solids dissolved. The resulting gadolinium chloride solution was added dropwise to the ligand and the mixture was vigorously stirred while maintaining a pH of 6–7 with 1N sodium hydroxide. After the addition was complete, the pH was adjusted to 7.4 with 1N sodium hydroxide to give an aqueous solution of gadolinium (III)-4-pentylbicyclo[2.2.2]octane-1-carboxyl-L-aspartyl-L-aspartyl-4-aminobutyl-diethylenetriaminepentaacetic acid. MS consistent.

Although the invention has been described with respect to specific modifications, the details thereof are not to be construed as limitations, for it will be apparent that various equivalents, changes and modifications may be resorted to without departing from the spirit and scope thereof, and it is understood that such equivalent embodiments are to be included therein.

What is claimed is:

1. The composition comprising a metal complex of the formula:

A—L—B—M      (I)

wherein A is selected from the group or derivatives of the group consisting of bicyclo[2.2.2]octane, adamantane, and dicyclohexylacetyl; L is a linker between A and B corresponding to a group of formula (II):

in which n is an integer from about zero to about 6; $R_1$, $R_2$ and $R_3$ may be the same or different and are hydrogen or —(CH$_2$)$_m$—X; m is an integer from about zero to about 6; X is hydrogen, —NH$_2$, —CO$_2$H, —SO$_3$H or —PO$_3$H$_2$; B is a chelating agent of metal ions M; and M is a metal ion having an atomic number selected from the set of numbers 22 through 29, 42 through 44 and 58 through 70.

2. The composition of claim 1 wherein A is 4-pentylbicyclo[2.2.2]octane-1-carbonyl-; $R_1$ is H; $R_2$ is H; $R_3$ is —CH$_2$CO$_2$H; n is 2; B is 4-aminobutyl-diethylenetriaminepentaacetic acid; and M is gadolinium (III).

3. The composition of claim 1 therein A is 3-carboxyadamantane -1-carbonyl-; n is 0; B is 4-aminobutyl-diethylenetriaminepentaacetic acid; and M is gadolinium (III).

4. The composition of claim 1 wherein A is dicyclohexylacetyl-; $R_1$ is H; $R_2$ is H; $R_3$ is —CH$_2$CO$_2$H; n is 1; B is 4-aminobutyl-diethylenetriaminepentaacetic acid; and M is gadolinium(III).

5. The composition of claim 1 wherein A is 4-pentylbicyclo[2.2.2]octane-1-carbonyl; $R_1$ is —H; $R_2$ is H; $R_3$ is —CH$_2$CO$_2$H; n is 2; B is 4-aminobutyl-1,4,7,10-tetraazacylododecane-1,4,7,10 tetraaceticacid; and M is gadolinium(III).

6. The composition of claim 1 wherein A is 4-pentylbicyclo[2.2.2]octane-1-carbonyl; $R_1$ is —CH$_3$; $R_2$ is H; $R_3$ is —CH$_2$CO$_2$H; n is 2; B is 4-N methyl aminobutyl-diethylenetriaminepentaacetic acid; and M is gadolinium (III).

7. A method of imaging a patient comprising administering a metal complex composition of the formula:

A—L—B—M      (I)

wherein A is selected from the group or derivatives of the group consisting of bicyclo[2.2.2]octane, adamantane, and dicyclohexylacetyl; L is a linker between A and B corresponding to a group of formula (II):

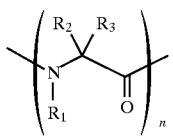

in which n is an integer from about zero to about 6; $R_1$, $R_2$ and $R_3$ may be the same or different and are hydrogen or —$(CH_2)_m$—X; m is an integer from about zero to about 6; X is hydrogen, —$NH_2$, —$CO_2H$, —$SO_3H$ or —$PO_3H_2$; B is a chelating agent of metal ions M; and M is a metal ion having an atomic number selected from the set of numbers 22 through 29, 42 through 44 and 58 through 70 and obtaining an image.

8. The method of claim 7 wherein A is 4-pentylbicyclo [2.2.2]octane-1-carbonyl-; $R_1$ is H; $R_2$ is H; $R_3$ is —$CH_2CO_2H$; n is 2; B is 4-aminobutyl-diethylenetriaminepentaacetic acid; and M is gadolinium (III).

9. The method of claim 7 wherein A is 3-carboxy-adamantane -1-carbonyl-; n is 0; B is 4-aminobutyl-diethylenetriaminepentaacetic acid; and M is gadolinium (III).

10. The method of claim 7 wherein A is dicyclohexylacetyl-; $R_1$ is H; $R_2$ is H; $R_3$ is —$CH_2CO_2H$; n is 1; B is 4-aminobutyl-diethylenetriaminepentaacetic acid; and M is gadolinium(III).

11. The method of claim 7 wherein A is 4-pentylbicyclo [2.2.2]octane-1-carboryl; $R_1$ is —H; $R_2$ is H; $R_3$ is —$CH_2CO_2H$; n is 2; B is 4-aminobutyl-1,4,7,10-tetraazacylododecane-1,4,7,10 tetraaceticacid; and M is gadolinium(III).

12. The method of claim 7 wherein A is 4-pentylbicyclo [2.2.2]octane-1-carbonyl; $R_1$ is —$CH_3$; $R_2$ is H; $R_3$ is —$CH_2CO_2H$; n is 2; B is 4-N methyl-aminobutyl-diethylenetriaminepentaacetic acid; and M is gadolinium (III).

* * * * *